(12) United States Patent
Kelly

(10) Patent No.: US 8,591,959 B1
(45) Date of Patent: Nov. 26, 2013

(54) BODY SPRITZER FORMULATION AND APPLICATION PROCESS

(76) Inventor: Angel Dayna Kelly, Las Vegas, NV (US)

(*) Notice: Subject to any disclaimer, the term of this patent is extended or adjusted under 35 U.S.C. 154(b) by 636 days.

(21) Appl. No.: 11/692,106

(22) Filed: Mar. 27, 2007

(51) Int. Cl.
*A61K 36/00* (2006.01)

(52) U.S. Cl.
USPC .............................. 424/725; 424/750; 424/776

(58) Field of Classification Search
None
See application file for complete search history.

(56) References Cited

U.S. PATENT DOCUMENTS

| | | | |
|---|---|---|---|
| 3,046,199 A | 7/1962 | Suzuki | |
| 4,224,339 A | 9/1980 | Van Scott et al. | |
| 4,438,099 A | 3/1984 | Azzariti | |
| 4,849,211 A | 7/1989 | Schrauzer | |
| 5,057,320 A * | 10/1991 | Evans et al. | 424/447 |
| 5,098,693 A | 3/1992 | Faas, Jr. et al. | |
| 5,759,559 A | 6/1998 | Fitzjarrell | |
| 5,928,631 A | 7/1999 | Lucas et al. | |
| 6,214,351 B1 * | 4/2001 | Wadsworth et al. | 424/769 |
| 6,558,682 B2 | 5/2003 | Yen et al. | |
| 6,808,717 B1 | 10/2004 | Bale | |
| 2004/0247542 A1 * | 12/2004 | Horino | 424/59 |

FOREIGN PATENT DOCUMENTS

| | | |
|---|---|---|
| ES | 8602403 | 3/1986 |
| GB | 354.417 | 8/1931 |
| JP | 2004275557 | * 10/2004 |
| JP | 2005082481 | * 3/2005 |
| WO | WO85/03225 | 8/1985 |

OTHER PUBLICATIONS

Wong. Which Massage Oil is Best?. About.com. Dec. 2, 2006. retrieved from the internet <http://altmedicine.about.com/od/massage/a/massage_oil.htm>. Retrieved on Oct. 16, 2009.*
Wacky Uses. Wesson Corn oil. May 8, 1999. Retrieved from the internet. <http://web.archive.org/web/19990508124850/http://www.wackyuses.com/wesson.html>. Retrieved on Oct. 15, 2009.*
Drugs.com. Retrieved from the internet. <http://www.drugs.com/nnp/jojoba.html>. Retrieved on Feb. 23, 2010. 3 pages.*
Squaleneoilproducts.com. Retrieved from the internet. Retrieved on Sep. 10, 2011. Web archive date Apr. 4, 2004. <http://web.archive.org/web/20040404195011/http://squaleneoilproducts.com/>. 1 page.*
yourdictionary.com. Retrieved from the internet on Mar. 7, 2012. <http://www.yourdictionary.com/spritz>. 1 page.*
macmilliandictionary.com. Retrieved from the internet on Mar. 7, 2012. <http://www.macmillandictionary.com/dictionary/american/spritz>. 1 page.*

* cited by examiner

*Primary Examiner* — Chris R Tate
(74) *Attorney, Agent, or Firm* — Michael I. Kroll

(57) ABSTRACT

A unique conditioning spritzer formula that presents improved skin qualities that can be used as a stand alone product on either wet or dry skin, or be applied in conjunction with another skin conditioner. The formula is made of purified water, jojoba oil, sesame seed oil, apricot oil, corn oil, squalene, and dibutyl hydroxytoluene.

2 Claims, 8 Drawing Sheets

42

ADDITIONAL METHOD OF APPLICATION FOR THE SKIN SPRITZER IN CONJUNCTION WITH USING THE BODY CONDITIONER OF THE PRESENT INVENTION ON DRY SKIN

- WET AND WASH BODY UTILIZING SHOWER OR BATH — S1
- CLEAN BODY WITH SHOWER GEL USING A LOOFA, A WASH CLOTH OR GLOVES, RINSE BODY THOROUGHLY — S2
- APPLY BODY CONDITIONER ONTO DESIRED AREA(S) OF WET SKIN — S3
- RINSE BODY CONDITIONER FROM AFFECTED AREA(S) OF BODY — S4
- PAT BODY DRY OR WIPE BODY DRY WITH TOWEL — S5
- LIGHTLY SPRAY SPRITZER OF PRESENT INVENTION ONTO DESIRED AREA(S) OF DRY SKIN — S6
- RUB SPRITZER INTO APPLIED AREA(S) OF DRY SKIN — S7

BENEFITS OF THE SKIN SPRITZER OF THE PRESENT INVENTION

- ADDS OIL TO SOOTHE AND MOISTURIZE THE SKIN
- DELICATELY ELIMINATES DRY SKIN FLAKES
- RESTORES SKIN VIGOR AND SMOOTH LOOK
- IMPROVES SKINS ABILITY TO BREATHE FRESH AIR
- REDUCES DRY SKIN EFFECT DUE TO SEASONAL WEATHER CONDITIONS
- INCREASES THE BODY'S ABILITY TO KEEP SKIN MOIST AND SOFT BETWEEN SHOWERING OR BATHING

FIG. 8

BODY SPRITZER FORMULATION AND APPLICATION PROCESS

BACKGROUND OF THE INVENTION

1. Field of the Invention

The present invention relates generally to skin conditioners and, more specifically, to a skin spritzer with a unique formulation and application processes.

The present invention is a skin spritzer comprising a unique formula that provides improved skin qualities. The present invention is also comprised of four (4) specific application methods.

The formulation of the body conditioner consists of the following components; purified water, jojoba oil, sesame seed oil, apricot oil, corn oil, squalene, and dibutyl hydroxytoluene.

The skin spritzer of the present invention is comprised of four (4) specific application methods. One application method is applied to wet skin after bathing or showering, while another application method is applied to dry skin after toweling off from a bath or shower. Additionally, the skin spritzer of the present invention may be applied in conjunction with another body conditioner in either wet or dry skin conditions.

On wet skin, the skin spritzer is applied to desired areas of the body and rubbed into the wet skin with excess to be showered off. Lastly the body is to be patted dry after getting out of the shower or bath. When used in conjunction with a body conditioner, the body conditioner is applied prior to the skin spritzer, the body conditioner is allowed to set for a period of time and rinsed off. The skin spritzer is then applied.

On dry skin, the skin spritzer is applied to desired areas of the body and rubbed into the skin. Lastly the body is to be patted dry. When used in conjunction with a body conditioner, the body conditioner is applied prior to the skin spritzer, the body conditioner is allowed to set for a period of time and rinsed off. After drying off the body, the skin spritzer is then applied.

The skin spritzer of the present invention provides a plurality of benefits to the bodily skin. Such benefits include delicately eliminating dry skin flakes, restoring skin to a vigor and smooth look, improving the skin's ability to breathe fresh air, reducing dry skin effect due to seasonally conditions, and increasing the body's ability to keep skin moist and soft between showering or bathing.

2. Description of the Prior Art

There are other bath/body lotions and sprays designed for improving skin conditions. Typical of these is U.S. Pat. No. 3,046,199 issued to Suzuki on Jul. 24, 1962.

Another patent was issued to Van Scott, et al. on Sep. 23, 1980 as U.S. Pat. No. 4,224,339. Yet another U.S. Pat. No. 4,438,099 was issued to Azzariti on Mar. 20, 1984 and still yet another was issued on Jul. 18, 1989 to Schrauzer as U.S. Pat. No. 4,849,211.

Another patent was issued to Faas, Jr., et al. on Mar. 24, 1992 as U.S. Pat. No. 5,098,693. Yet another U.S. Pat. No. 5,759,559 was issued to Fitzjarrell on Jun. 2, 1998. Another was issued to Lucas, et al. on Jul. 27, 1999 as U.S. Pat. No. 5,928,631 and still yet another was issued on May 6, 2003 to Yen, et al. as U.S. Pat. No. 6,558,682.

Another patent was issued to Bale on Oct. 26, 2004 as U.S. Pat. No. 6,808,717. Yet another U.K. Patent No. GB 354,417 was issued to Bubbury, et al. on Aug. 13, 1931. Another was issued to Saint-Leger, et al. on Aug. 1, 1985 as International Patent Application No. WO85/03225 and still yet another was issued on Mar. 16, 1986 to Kao Corp. as Spain Patent No. ES8602403.

U.S. Pat. No. 3,046,199

Inventor: Tsuneshi Suzuki

Issued: Jul. 24, 1962

A cosmetic composition being useful for facial treatments, said composition, said composition comprising from 0.1% to 0.2% by weight of scordine and from 0.01% to 0.1% by weight of 4,4,4-trimethyl-3,3,3-triheptyl-8(2-thiazol)-2,2-pentamethin thiazolocyanin-2,3-diiodide together with from 4% to 12% by weight of a propellant selected from the group consisting of dichlorodifluoromethane, di-chlorotetrafluoro ethane and liquified petroleum gas.

U.S. Pat. No. 4,224,339

Inventor: Eugene J. Van Scott

Issued: Sep. 23, 1980

Preventive as well as therapeutic treatment to alleviate the symptoms of disturbed keratinization, consisting of the topical application of a solution, gel, lotion, cream, ointment, stick, powder or spray containing one or more cysteic acid compounds, is disclosed. The compounds include free acid, ammonium salt, amine salt, metal chelate and metallic salt forms of cysteic acid, cysteine sulfinic acid and homocysteic acid. The efficacious compositions may include the active ingredients present in a total amount of from 0.1 to 30 percent by weight. Topical application to affected areas has been found to achieve from a substantial to a complete remission of dry skin, keratoses, warts and palmar and plantar hyperkeratosis. Used as a hair dressing, the compositions have been found to give the hair excellent grooming and luster.

U.S. Pat. No. 4,438,099

Inventor: Vittorio Azzariti

Issued: Mar. 20, 1984

A spray of Candida kruseii is applied to the burned area of skin to allow for the healing of the burn and regeneration of the skin in the affected area. The Candida kruseii spray forms a crust over the affected area, allowing for a more rapid healing and skin regeneration in the affected area than is accomplished with prior burn control treatment. The Candida kruseii treatment is also effective with other open sores, such as varicose ulcers and decubitus ulcers.

U.S. Pat. No. 4,849,211

Inventor: Gerhard N. Schrauzer

Issued: Jul. 18, 1989

A composition comprising squalene and saturated normal aliphatic hydrocarbons which is very effective in the treatment of acne, minor skin irritations and minor skin wounds, burns, inflammation and soreness when applied topically to the skin. Basically, the product comprises from about 5 to 40 volume percent squalene and from about 5 to 25 volume percent n-decane, n-dodecane or mixtures thereof with the balance being normal aliphatic hydrocarbons with chain lengths in the C10 to C35 range or a water-polysorbate emulsion. If desired, certain other ingredients such as zinc oxide or a filler may be added to the mixture. The product may be applied as a spray, cream or gel.

U.S. Pat. No. 5,098,693

Inventor: Leonard A. Faas, II

Issued: Mar. 24, 1992

This invention concerns a novel method for eliminating skin irritation or "itching" within a cast by means of applying an anti-irritant aerosol spray to the skin within the cast. The anti-irritant spray includes talc and triclosan. The spray may also include isopropyl myristate and a fragrance additive as well as trichlorotrifluoroethane and SD alcohol 40.

U.S. Pat. No. 5,759,559

Inventor: Edwin A. Fitzjarrell

Issued: Jun. 2, 1998

A method and composition for treating outbreaks of acne. Initially, the acne affected area is cleaned. A topical spray comprising about 1 to 20 grams niacinamide per 100 grams solution in an inert carrier is then applied to the area. A composition that includes lysine, selenium, chromium and zinc and any desired vitamins and minerals is then taken orally in the form of a capsule or tablet. Generally, at least two spray applications are made and two capsules are taken each day. For optimum skin cleaning, an exfoliation scrub such as a conventional apricot facial scrub is applied to the skin prior to application of the niacinamide topical spray.

U.S. Pat. No. 5,928,631

Inventor: Juliet Marie Lucas

Issued: Jul. 27, 1999

The present invention encompasses a method of controlling environmental malodors on the body comprising the application to the skin of a composition comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, and skin protectants; one or more surfactants each having a hydrophilic/lipophilic balance of about 8 to 18 and wherein each surfactant, when combined with an aqueous cyclodextrin solution, provides no less than 25% of odor capture as an aqueous cyclodextrin solution; and an aqueous carrier. The compositions can be applied directly as a spray, poured from a bottle and applied by hand, or applied via a wipe.

U.S. Pat. No. 6,558,682

Inventor: Helen Shu Ying Yen

Issued: May 6, 2003

The present invention relates to substantially uniform, discontinuous films of a skin care product having a defined average particle size, particle spacing and coverage value. The films provide improved skin appearance, e.g., good apparent coverage and a natural look. The films can be formed by any method which provides the defined particle size, particle spacing and coverage value, including silk screening and the like and electrostatic spray techniques. The films are preferably formed by electrostatically spraying the composition onto the skin.

U.S. Pat. No. 6,808,717

Inventor: Isidore Bale

Issued: Oct. 26, 2004

A composition of an aerosol coolant spray for killing and removing ticks from human skin, to be dispensed from a pressurized a pressurized aerosol spray cannister. The aerosol coolant spray composition includes a liquid coolant material for freezing the essential oil, and the cooled essential oil is used for immobilizing and killing the tick on the skin of a human. The aerosol coolant spray composition further includes a diluent material being used as a carrier material for emulsifying the essential oil and the coolant material within the pressurized aerosol spray cannister.

U.K. Patent Number GB 354,417

Inventor: Hugh Mills Bunbury, et al

Issued: Aug. 13, 1931

Sulphonated products suitable for use in the textile, rubber, and leather industries, particularly as emulsifying agents are obtained by treating squalene or an oil containing squalene e.g. fish liver oils with sulphuric acid or oleum at a temperature not exceeding 60 DEG C., in the presence or absence of an organic acid anhydride. In examples, squalene and shark liver oil are treated with sulphuric acid, oleum, and also with a mixture of sulphuric acid and acetic anhydride, whilst cooling. The product obtained by sulphonating shark liver oil with sulphuric mono hydrate gives an emulsion with water, benzene, and glue. An emulsion suitable as an insecticidal and fungicidal spray is prepared from the same sulphonated product; glue and a neutral tar oil.ALSO:Sulphonated products suitable for use in the textile, rubber and leather industries, particularly as emulsifying agents are obtained by treating squalene or an oil containing squalene, e.g. shark liver oils, with sulphuric acid or oleum at a temperature not exceeding 60 DEG C., in the presence or absence of an organic acid anhydride. In examples, shark liver oil is treated with sulphuric acid, oleum and also with a mixture of sulphuric acid and acetic anhydride, whilst cooling. The product is isolated by adding benzene, washing with brine to remove the excess of acid and finally freeing the solution of oil from the solvent. In a further example, squalene is sulphonated with sulphuric acid. The product obtained by sulphonating shark liver oil with monohydrate gives an emulsion with water, benzene and glue. An emulsion suitable as an insecticidal and fungicidal spray is prepared from the same sulphonated product, glue and a neutral tar oil.ALSO:An emulsion suitable as an insecticidal and fungicidal spray is prepared from glue, a neutral tar oil and a product obtained by sulphonating shark liver oil containing 70 percent of squalene, with sulphuric acid.

International Patent Application Number WO 85/03225

Inventor: Didier Saint-Leger, et al

Issued: Aug. 1, 1985

The composition contains as a main active principle in a pharmaceutically acceptable carrier at least one substance pertaining to the family of carotenoids and selected particularly in the group comprised of beta-carotene-alpha-carotene, delta-carotene, gamma-carotene, beta, beta-carotene-4,4'-dione, 8'-epo, beta-carotene-8'-oate of ethyl, beta-epo-8'-carotenal, psi, psi-carotene, psi, psi-carotene-16,16'-diol and psi, psi-carotene-16-ol. Preferably said composition contains from 0.001 to 10% by weight of active principle based on the total weight of the composition and has the form of a cream, a milk, a gel, a lotion, a stick, a foam or a spray. The pharmacological activity of this medicinal composition is an inhibiting activity of the formation of comedones which are due to an irritation caused by an excess of oxide of lipides (oxidized squalene).

Spain Patent Number ES8602403

Inventor: KAO Corp

Issued: Mar. 16, 1986

Agents for cleansing and wiping the skin, comprising jojoba oil, natural squalane and/or glycerol tri-2-ethylhexanoate . . . . The specified oils can be used as such or in combination with a silicone oil. The agents may if desired contain a microbicide, a pharmacologically active substance (e.g. an antiinflammatory agent), aroma substances, etc. . . . Pref. formulations are sprays for application to toilet or tissue paper used for wiping the circum-anal region. The spray may alternatively be applied directly to the circum-anal region before wiping with normal toilet paper. The agents may alternatively be in the form of an impregnated material, pref. paper or lint.

While these bath/body lotions and sprays may be suitable for the purposes for which they were designed, they would not be as suitable for the purposes of the present invention, as hereinafter described.

SUMMARY OF THE PRESENT INVENTION

A primary object of the present invention is to provide a skin spritzer utilizing a unique formulation.

Another object of the present invention is to provide a skin spritzer application method on wet skin.

Yet another object of the present invention is to provide a skin spritzer application method on dry skin.

Still yet another object of the present invention is to provide a skin spritzer that is a self supporting body treatment.

Another object of the present invention is to provide a skin spritzer that may be used in conjunction with a body conditioner.

Yet another object of the present invention is to provide a skin spritzer that is a self supporting body treatment that is patted dry from the body after application.

Yet another object of the present invention is to provide a skin spritzer that delicately eliminating dry skin flakes.

Another object of the present invention is to provide a skin spritzer that restores skin to a vigor and smooth look.

Still yet another object of the present invention is to provide a skin spritzer that improves the skin's ability to breathe fresh air.

Yet another object of the present invention is to provide a skin spritzer that reduces dry skin effect due to seasonally conditions.

Still yet another object of the present invention is to provide a skin spritzer that increases the body's ability to keep skin moist and soft between showering or bathing.

Additional objects of the present invention will appear as the description proceeds.

The present invention overcomes the shortcomings of the prior art by providing a unique formula that presents improved skin qualities that can be used as a stand alone product on either wet or dry skin, or be applied in conjunction with another skin conditioner.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which:

FIG. 7 is a block diagram of the present invention's skin spritzer with body conditioner application method on dry skin; and FIG. 8 is a block diagram of the benefits for the present invention's skin spritzer.

Figure 1:
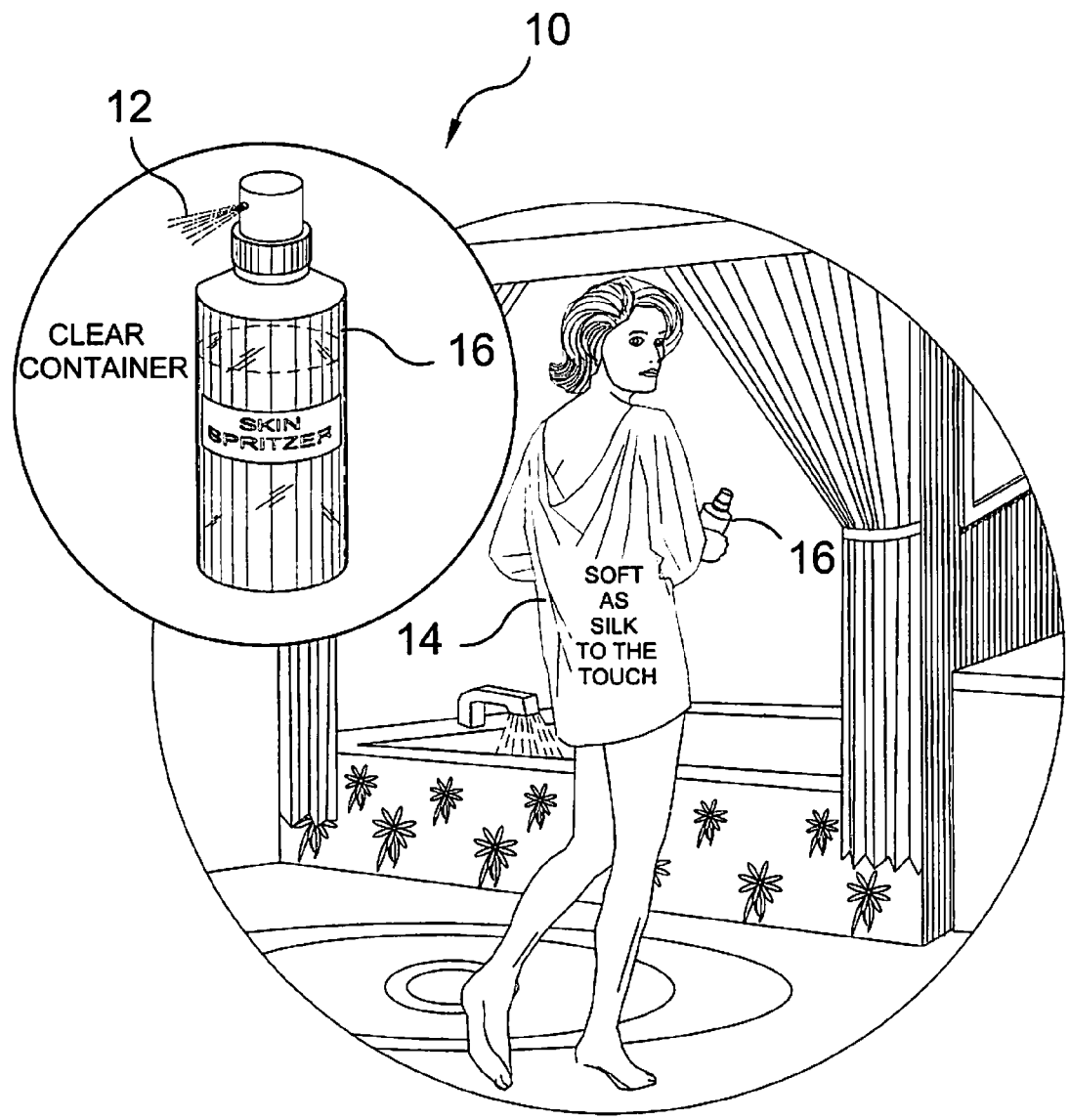
FIG. 1 is an illustrative view of the present invention's skin spritzer in use.

Turning now descriptively to the drawings, in which similar reference characters denote similar elements throughout the several views, the Figures illustrate the Body Spritzer Formulation and Application Process of the present invention. With regard to the reference numerals used, the following numbering is used throughout the various drawing figures.

10 Body Spritzer Formula and Application Process
12 skin spritzer formulation
14 user
16 pump spritzer container 18 purified water
20 jojoba oil
22 sesame seed oil
24 apricot oil
26 corn oil
28 squalene
30 dibutyl hydroxytoluene
32 application method
34 wet skin application
36 dry skin application
38 self-supporting application
40 combination application
42 benefits of using skin spritzer formulation

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present invention 10 in use. The present invention 10 is a skin spritzer formulation 12 and process of application comprising a unique formula 12 that provides improved skin qualities. Shown is the user 14 using the pump spray container 16 for the application thereof. The present invention 10 also comprises four (4) specific application methods.

Figure 2:
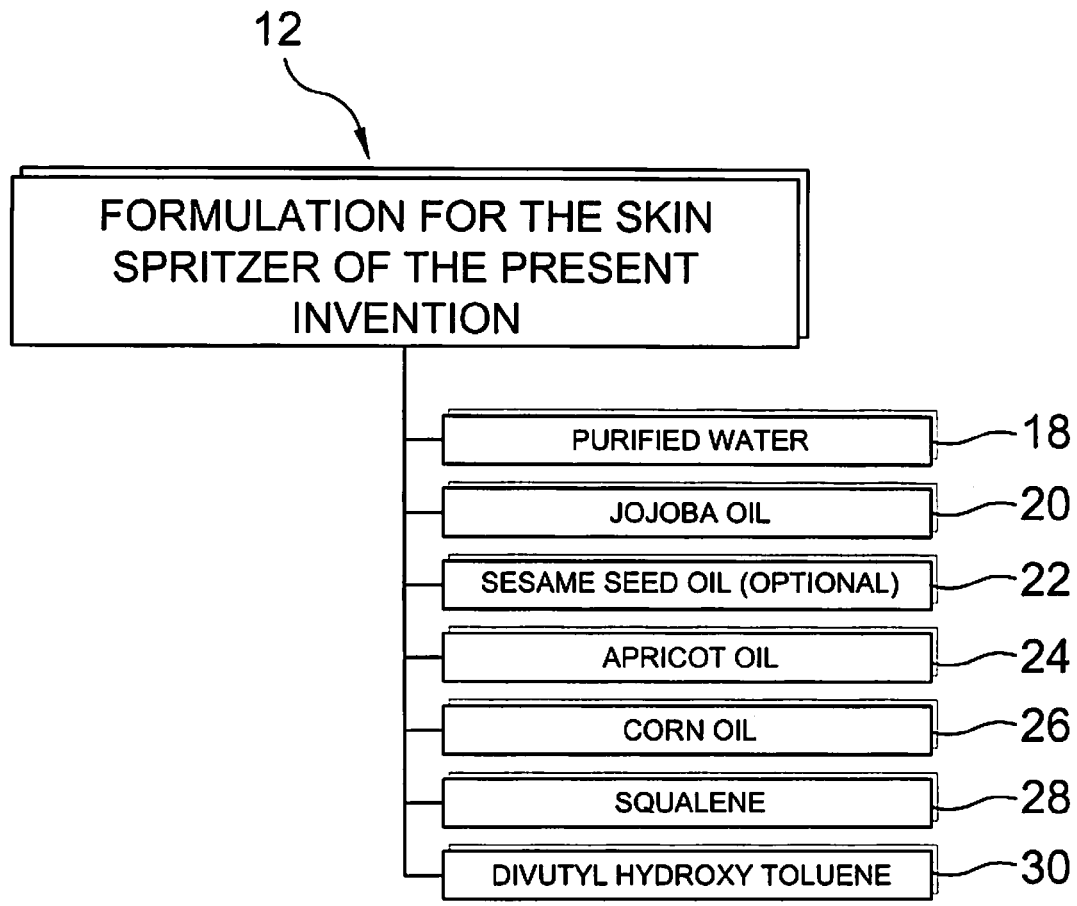
FIG. 2 is a block diagram of the present invention's skin spritzer formulation.

FIG. 2 is a block diagram of the present invention's skin spritzer formulation 12. The skin spritzer formula is a unique formula 12 comprising purified water 18, jojoba oil 20, apricot oil 24, corn oil 26, squalene 28 and dibutyl hydroxytoluene 30. The formula 12 may also include sesame oil 22 a warning must be on any packaging or container to alert people allergic to nuts or any by-product of nuts.

Figure 3:
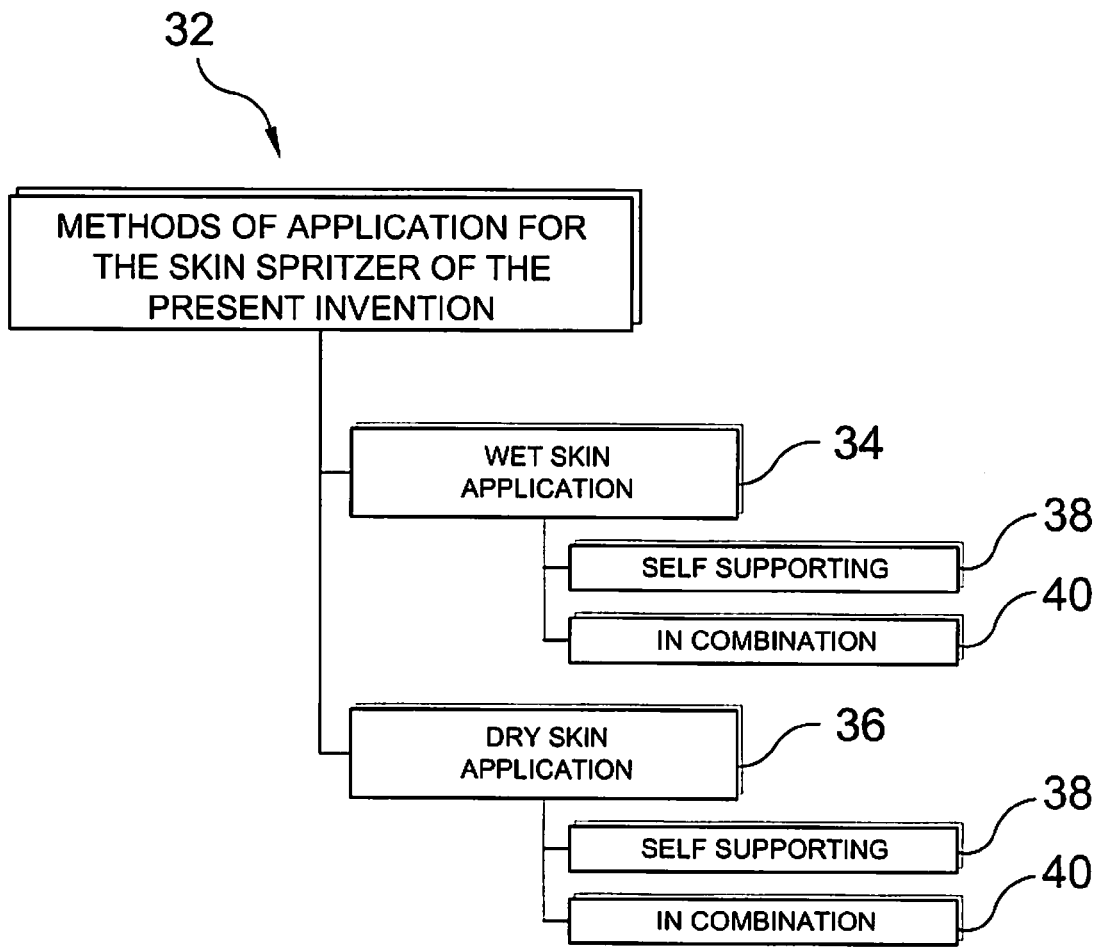
FIG. 3 is a block diagram of the present invention's skin spritzer application methods.

FIG. 3 is a block diagram of the present invention's skin spritzer application methods 32. The skin spritzer of the present invention comprises four (4) specific application methods 32. The skin spritzer can be applied to either dry skin 36 or to wet skin 34. Additionally the skin spritzer may be applied alone 38 or in combination with a body conditioner 40.

Figure 4:
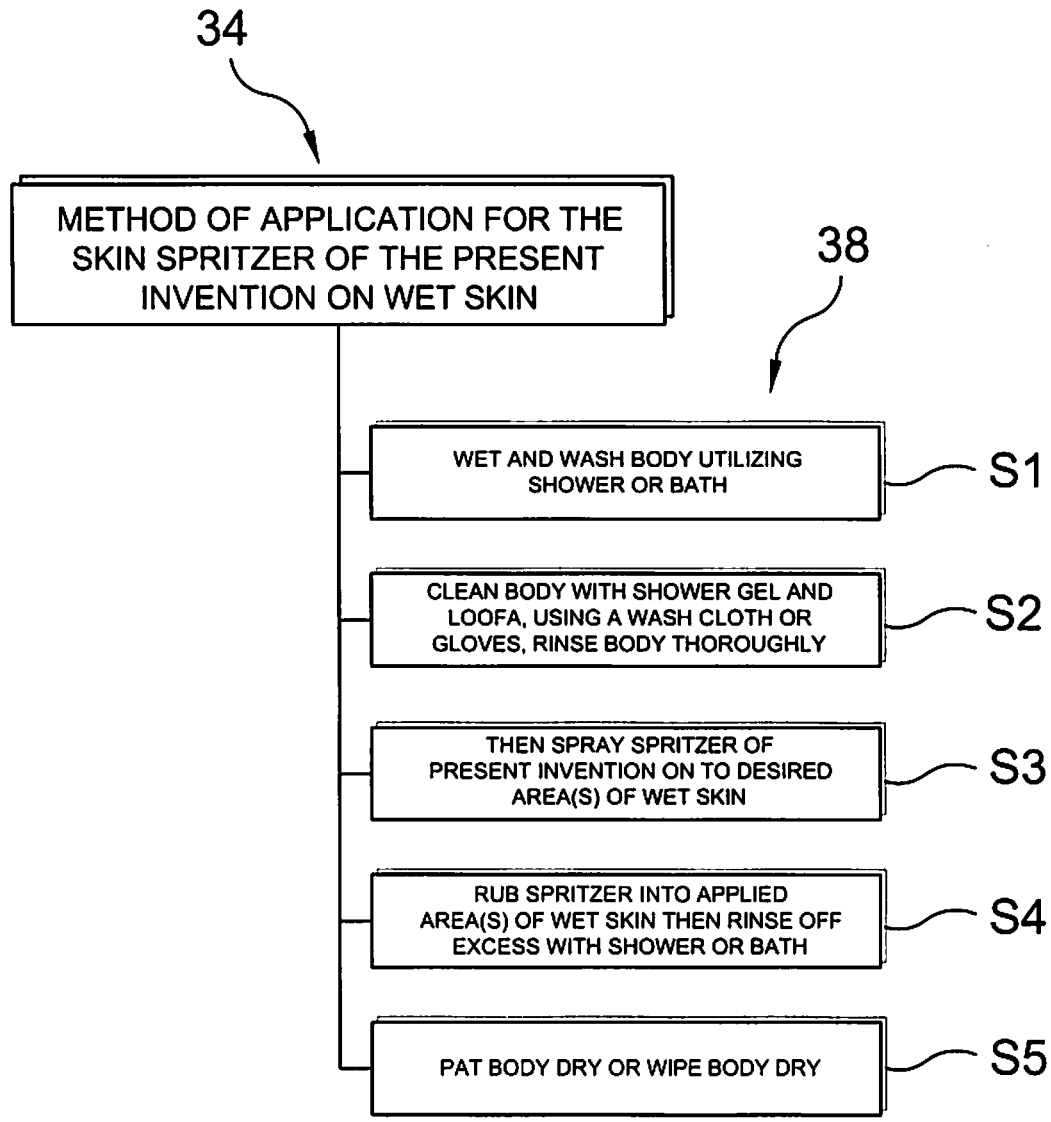
FIG. 4 is a block diagram of the present invention's skin spritzer application method on wet skin.

FIG. 4 is a block diagram of the present invention's skin spritzer application method on wet skin 34 during a self-supporting application 38. The wet skin application method 34 involves the steps of: wetting and washing the body utilizing a shower or bath; cleaning the body with shower gel and loofa, wash cloth or gloves then rinsing the body thoroughly; spraying the formula onto the desired areas of the wet skin (but never to the bottom of the feet which makes them slippery and could present a hazard); rubbing the formula into applied areas and then rinsing off the excess in a shower or bath; and patting or wiping the body dry.

Figure 5:
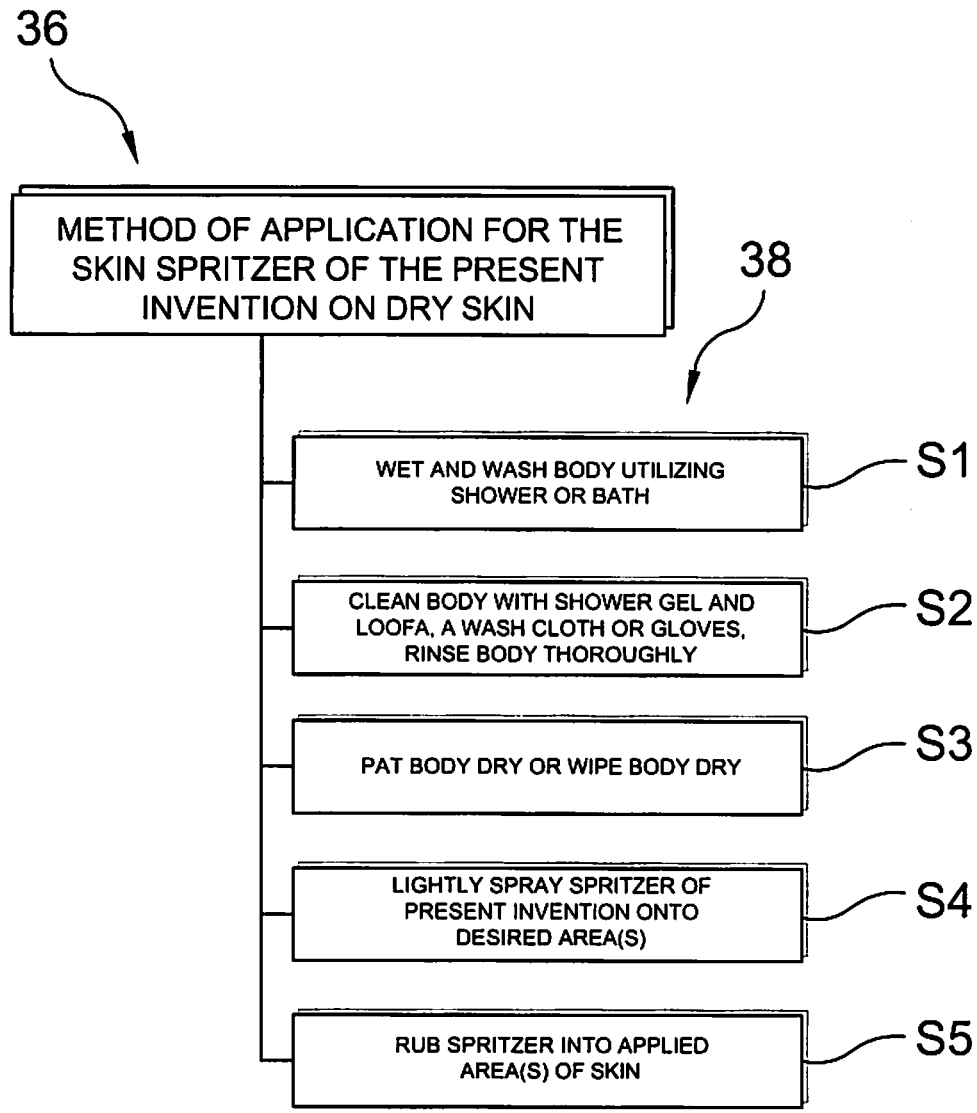
FIG. 5 is a block diagram of the present invention's skin spritzer application method on dry skin.

FIG. 5 is a block diagram of the present invention's skin spritzer application method on dry skin 36 during a self-supporting application 38. The dry skin application method 36 involves the steps of: wetting and washing the body utilizing a shower or bath; cleaning the body with shower gel and loofa, wash cloth or gloves then rinsing the body thoroughly; patting or wiping the body dry; spraying the formula onto the desired areas of the wet skin (but never to the bottom of the feet which makes them slippery and could present a hazard); rubbing the formula into applied areas and then rinsing of the excess in a shower or bath; and patting or wiping the body dry.

Figure 6:
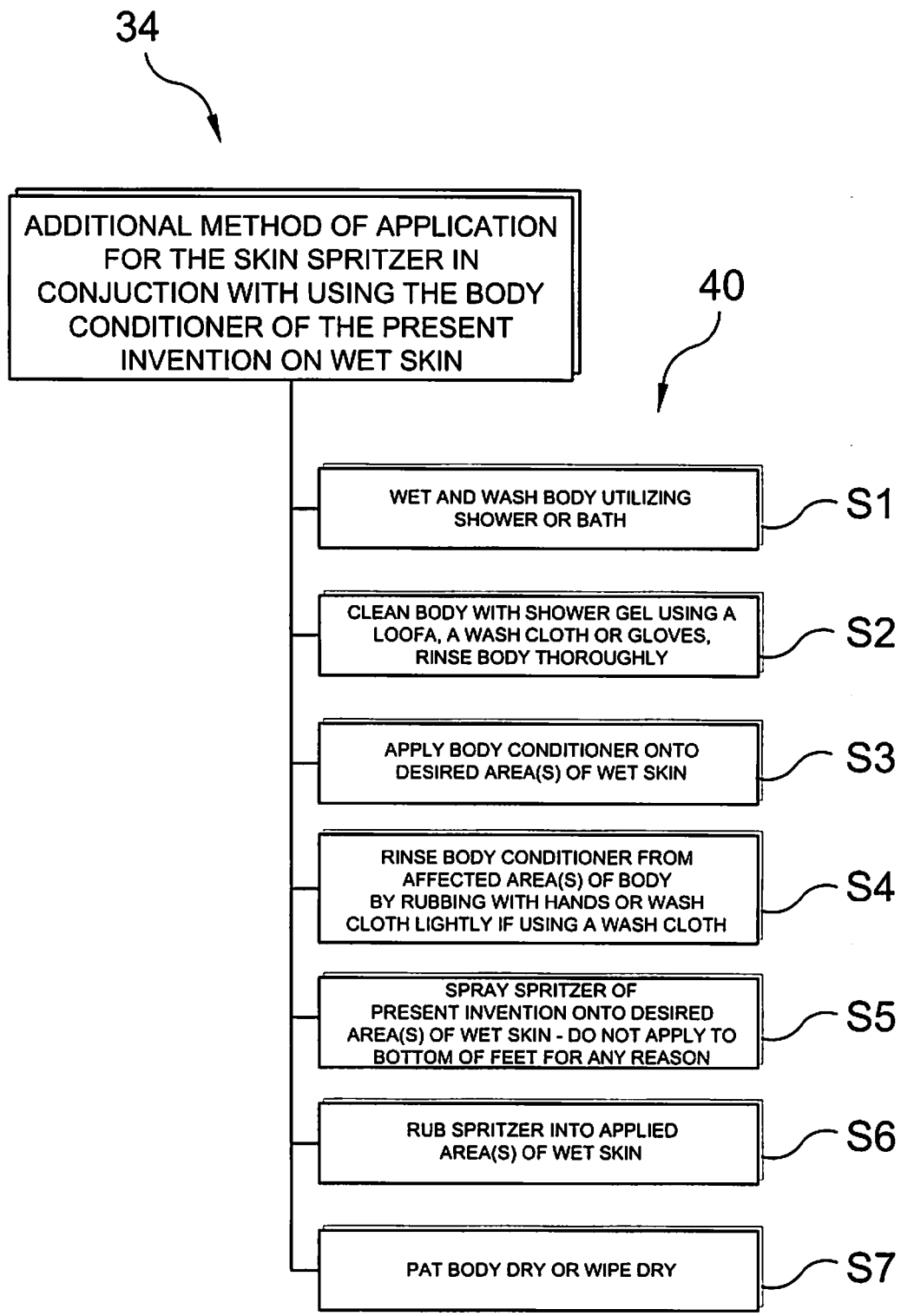
FIG. 6 is a block diagram of the present invention's skin spritzer with body conditioner application method on wet skin.

FIG. 6 is a block diagram of the present invention's skin spritzer application method on wet skin 34 in combination with a body conditioner 40. The wet skin application method 34 in combination with body conditioner 40 involves the steps of: wetting and washing the body utilizing a shower or bath; cleaning the body with shower gel and loofa, wash cloth or gloves then rinsing the body thoroughly; applying body conditioner onto desired areas of wet skin; rinsing the body conditioner from affected areas of the body by rubbing with hands or was cloth lightly if using a wash cloth; spraying the formula onto the desired areas of the wet skin (but never to the bottom of the feet which makes them slippery and could present a hazard); rubbing the formula into applied areas and then rinsing of the excess in a shower or bath; and patting or wiping the body dry.

FIG. 7 is a block diagram of the present invention's skin spritzer application method on dry skin 36 in combination with a body conditioner 40. The dry skin application method 36 in combination with body conditioner 40 involves the steps of: wetting and washing the body utilizing a shower or bath; cleaning the body with shower gel and loofa, wash cloth or gloves then rinsing the body thoroughly; applying body conditioner onto desired areas of dry skin; rinsing the body conditioner from affected areas of the body by rubbing with hands or wash cloth lightly if using a wash cloth; patting or wiping the body dry; spraying the formula onto the desired areas of the wet skin (but never to the bottom of the feet which makes them slippery and could present a hazard); rubbing the formula into applied areas and then rinsing of the excess in a shower or bath; and patting or wiping the body dry.

FIG. 8 is a block diagram of the benefits 42 for the present invention's skin spritzer. The skin spritzer of the present invention provides a plurality of benefits to the bodily skin. Such benefits include delicately eliminating dry skin flakes, restoring skin to a vigor and smooth look, improving the skins ability to breathe fresh air, reducing dry skin effect due to seasonally conditions, and increasing the body's ability to keep skin moist and soft between showering or bathing.

What is claimed is new and desired to be protected by Letters Patent is set forth in the appended claims:

1. A skin conditioning formulation contained within a pump-spray container, wherein said formulation consists of a spritz fluid made up of suitable amounts of the following ingredients:
   a) purified water;
   b) jojoba oil;
   c) apricot oil;
   d) corn oil;
   e) squalene;
   f) dibutyl hydroxyl toluene; and
   g) sesame oil.

2. A method for conditioning the skin of a subject comprising spraying the formulation of claim 1 onto specific epidermal surfaces of the subject's body.

* * * * *